United States Patent
Buijs et al.

[11] Patent Number: 5,210,331
[45] Date of Patent: May 11, 1993

[54] METHOD FOR THE PREPARATION OF A PHENOL

[75] Inventors: Wim Buijs, Schinnen; Leon H. B. Frijns, Valkenburg; Matthias R. J. Offermanns, Munstergeleen, all of Netherlands

[73] Assignee: DSM NV, Heerlen, Netherlands

[21] Appl. No.: 814,875

[22] Filed: Dec. 31, 1991

Related U.S. Application Data

[63] Continuation-in-part of Ser. No. 724,173, Jul. 1, 1991, abandoned, which is a continuation of Ser. No. 626,639, Dec. 12, 1990, abandoned.

[30] Foreign Application Priority Data

Dec. 19, 1989 [NL] Netherlands ............... 8903098
Jun. 14, 1991 [BE] Belgium ............... 09100579
Jun. 14, 1991 [BE] Belgium ............... 09100582
Jun. 14, 1991 [BE] Belgium ............... 09100583

[51] Int. Cl.⁵ ............................................. C07C 37/56
[52] U.S. Cl. .................................... 568/801; 568/800; 568/802
[58] Field of Search .................. 568/800, 801, 802

[56] References Cited

U.S. PATENT DOCUMENTS

| | | | |
|---|---|---|---|
| 2,766,294 | 10/1956 | Toland | 568/801 |
| 2,852,567 | 9/1958 | Barnard | 568/801 |
| 3,803,247 | 4/1974 | Glew | 568/801 |
| 3,929,911 | 12/1975 | van Dierendonck et al. | 568/801 |
| 4,154,964 | 5/1979 | Balg | 568/757 |
| 4,405,823 | 9/1983 | Maki | 568/801 |

FOREIGN PATENT DOCUMENTS

0434140 6/1991 European Pat. Off. .

Primary Examiner—Werren B. Lone
Attorney, Agent, or Firm—Cushman, Darby & Cushman

[57] ABSTRACT

The invention relates to a process for the preparation of a phenol by oxidative decarboxylation of a corresponding arylcarboxylic acid in the presence of a Cu-containing catalyst, the phenol being obtained through a hydrolysis step. The characteristic part of the process is oxidation of a Cu(I)-containing catalyst and reduction and hydrolysis in the absence of oxygen. The process can be carried out under liquid phase or gas phase conditions in a one-step or multi-step process and nucleation agents can be added for crystallization during catalyst oxidation. In a preferred embodiment, at least 0.04 wt.% copper remains present as Cu(I) after oxidation.

39 Claims, 1 Drawing Sheet

METHOD FOR THE PREPARATION OF A PHENOL

This is a continuation-in-part application of Ser. No. 724,173 filed Jul. 1, 1991 now abandoned which in turn is a continuation application of Ser. No. 626,639 filed Dec. 12, 1990, now abandoned, the contents of which are incorporated by reference.

This invention relates broadly to a process for the preparation of a phenol by oxidative decarboxylation of a corresponding arylcarboxylic acid in the presence of a Cu-containing catalyst.

In one aspect, the invention relates to a method for the preparation of a phenol by oxidative decarboxylation in the liquid phase of the corresponding arylcarboxylic acid in the presence of a dissolved Cu-containing catalyst, the phenol being obtained through a hydrolysis step.

In another aspect, the invention relates to a process for the preparation of a phenol by an oxidative decarboxylation in the gas phase of a corresponding arylcarboxylic acid in the presence of a Cu-containing catalyst.

BACKGROUND OF THE INVENTION

The preparation of a phenol by an oxidative decarboxylation has been known for a long time. NL-B-90.684 already disclosed such a process, with oxidation, decarboxylation and hydrolysis all being carried out in one single process step, at a temperature of at least 200° C. and preferably 230°-250° C.

This so-called Dow phenol process has been the subject of a number of patent publications, which aimed to eliminate the major drawback of the above process, i.e. the formation of a considerable number of byproducts, mainly in the form of tar.

NL-A-70.00685, for instance, discloses a two-step process for the preparation of a phenol from a benzene monocarboxylic acid. First, oxidation and decarboxylation are simultaneously effected at a temperature of 230°-240° C. The corresponding phenyl benzoate obtained is subsequently hydrolysed in the presence of oxygen at a temperature of about 200° C.

NL-A-78.07199 describes a method for the preparation of a phenol on the basis of a three-step process. First an oxidation is carried out, in the absence of water, at a temperature of preferably 120°-170° C.; then a decarboxylation in the absence of oxygen and water, at a temperature of, preferably, lower than 220° C., and the third step comprises hydrolysis of the aryl benzoate obtained, carried out in the absence of oxygen and preferably at a temperature of about 220° C. According to the applicant of the above-mentioned patent, the presence of water in the decarboxylation is to be avoided, which is achieved by addition of a dehydrating agent, by an azeotropic distillation with an extra hydrocarbon added, or by stripping with a dry, inert gas.

With the aim of preventing tar formation it has been suggested to have the reaction take place in the gas phase on a solid copper-containing catalyst; see for instance NL-B-107561 and NL-B-110374. These, as well as later publications, which are mainly aimed at optimization of the catalyst (e.g. NL-A-7810528, EP-A-52839 and EP-A-40452), do not disclose systems whereby tar formation is actually suppressed, however. In all cases it appears that after some time the catalyst is covered with a black tar-like coat, which in particular affects its activity.

However, all the processes referred to have not been able to realize phenol formation at a high yield with little, if any, tar formation in an economically sound way.

According to NL-A-78.07199, for instance, a very large amount of catalyst is used, such that it takes the form of a separate, solid phase, rather than a homogeneous one, with all consequences thereof (including troublesome separation from the reaction mixture of the metal oxides formed). In addition, the methods employed to avoid the presence of water in the decarboxylation are rather expensive and laborious; the high yields cited cannot be reproduced.

SUMMARY OF THE INVENTION

Accordingly, an object of the invention is to provide an oxidative decarboxylation process for the formation of a high yield of a phenol product.

Another object of the invention is to provide an economical and efficient oxidative decarboxylation process for the formation of phenol in high yield with little, if any, tar formation.

Other objects, aspects as well as the several advantages of the invention will be apparent to those skilled in the art upon a study of the disclosure and appended claims.

In accordance with the invention, a process is provided for the production of a phenol in high yield and selectively with little, if any, tar formation which comprises the oxidative decarboxylation of an arylcarboxylic acid under either liquid phase or gas phase conditions and controlled temperatures above the melting point of the arylcarboxylic acid in the presence of a Cu-containing catalyst.

More specifically, according to the invention, oxidation of an arylcarboxylic acid and formation of a phenol is carried out [at] under oxidation conditions in the presence of a Cu-containing catalyst followed by hydrolysis and reduction of oxidized catalyst under liquid-phase or gas phase conditions in a one-step or multi-step process.

The method according to the invention provides a process for the preparation of a phenol from the corresponding arylcarboxylic acid in which the drawbacks encountered in the above-mentioned prior art methods are eliminated. Thus, a process is obtained in which high preparation selectivities are combined with economically attractive embodiments.

Generally, the process according to the invention is characterized in that the following are effected:
a) oxidation of the catalyst with the temperature, retention time, oxidation agent, phenol concentration and Cu(I) concentration being chosen so that virtually no tar is formed,
b) reaction of the oxidized catalyst of a) and formation of phenol in the absence of oxygen, but in the presence of water, and
c) separation of phenol and optionally recycling of the (reduced) catalyst to a).

The process according to a first embodiment of the invention is characterized in that the following process steps are carried out:
a) catalyst oxidation at a temperature of 120°-190° C.;
b) reaction of the aryl carboxylic acid in question with the oxidized catalyst of step a), carried out in the absence of oxygen and with the aid of water, at a temperature of 225°-270° C.;

c) separation of the phenol thus obtained and recycling of the (reduced) catalyst to step a).

The process according to a second embodiment of the invention is characterized in that the oxidative decarboxylation is carried out at a temperature higher than the first embodiment, for example, between 191°–270° C., with a sufficient amount of oxygen being added that some copper remains present as Cu(I) so that a selectivity to phenol of more than 92% measured at 1 bar is obtained.

This embodiment of the process can simply be carried out in a receptacle and continuously as a "one-step" process or as a "multi-step" process, if desired.

A virtually 100% selectivity is achieved in the second embodiment of the invention if the following process steps are carried out:
a) oxidation of the catalyst at a temperature of 191°–240° C., with such an amount of oxygen being added that at least 0.04 wt% copper remains present as Cu(I);
b) reaction of the oxidized catalyst of step a) and formation of the phenol in the absence of oxygen, but in the presence of water, at a temperature of 210°–270° C.;
c) separation of phenol and recycling of the (reduced) catalyst to step a).

By performing the process in this way, a two-step process is obtained: first an oxidation, then a reduction and formation of the phenol.

In this way the number of process steps is reduced in comparison with the process described in NL-A-78.07199. In addition it appears that the process according to the invention gives a higher yield with little, if any, tar formation.

The process according to a third embodiment of the invention is characterized in that the following process steps are carried out either in a single reaction zone or plural reaction zones in the gas phase:
a) supplying an oxidant-containing gas mixture to a catalyst bed under such conditions that tar formation is virtually absent, and
b) supplying arylcarboxylic acid and steam with exclusion of oxygen, resulting in formation of gaseous phenol.

By performing the process in this way, a two-step process is obtained: first an oxidation, then formation of the phenol in combination with reduction of the catalyst.

The process according to a fourth embodiment of the invention is characterized in that the following process steps are effected:
a) oxidation of the catalyst at a temperature of 120°–270° C., with the temperature, retention time, oxidation agent, phenol concentration and Cu(I) concentration being chosen so that virtually no tar is formed,
b) reaction of the oxidized catalyst of step a) and formation of phenol in the absence of oxygen, but in the presence of water, at a temperature of 210°–270° C., and
c) separation of phenol and recycling of the (reduced) catalyst to step a), wherein
4–10 wt.% Cu is present in the reaction mixture, in step a) such that the quantity of Cu(I) salt being converted to Cu(II) salt is higher than its solubility product and a slurry is formed in step a), adding nucleation agents in step a) for crystallization and carrying out step b) in a cascade of at least two reactors or reaction zones, the reduction of the catalyst being continued until a homogeneous solution is obtained.

DESCRIPTION OF DRAWINGS

A better understanding of the invention will be obtained upon referring to the drawings in which.

DETAILED DESCRIPTION OF THE INVENTION

By performing the process embodiments described herein, generally, a two-step process is obtained: first an oxidation, then combined (intermediate) formation of the arylcarboxylate (the reduction) and hydrolysis of this ester to the phenol. Combining the formation of the ester with the hydrolysis to the phenol has a strong positive effect on the overall yield. Also, the number of separate process steps is reduced in comparison with the process described in NL-A-78.07199. As described in connection with the second embodiment of the invention, the process can be carried out as a "one-step process". Of course, these process step (reduction and hydrolysis) according to the invention, under the conditions as outlined, can also be effected separately (which may make it possible to apply some variations in the reaction conditions for the reduction compared with those for hydrolysis), but the possibility to use one single reactor for the combined reactions is of greater advantage.

Here and below, arylcarboxylic acid is understood to be a compound having the following structure:

where $R_1$ through $R_5$ may be hydrogen (on the proviso that at least $R_1$ or $R_5$ is hydrogen) or the following groups, substituted or not, which have a so-called Hammett constant of between $-1$ and $+2$. A description of this Hammett ($\sigma$) value, which represents a measure of the influence of the group on the reactivity of the arylcarboxylic acid, can be found in J. March, Advanced Organic Chemistry 1989, pages 242–250; reference is made in particular to table 4 on page 244. The groups that can be used therefore are: $C_1$–$C_6$ alkyl, cycloakyl, aryl, arylalkyl, amino, halogen and nitro.

It is surprising that by the process according to the second embodiment of the invention, metanitrobenzoic acid is converted into p-nitrophenol with a selectivity of >99% (the o-nitrophenol was only present in the form of traces).

Salts, esters and anhydrides of (I) are also suitable, while groups may also be connected through a ring system, as is the case for instance in naphthalene carboxylic acid. Likewise, polyaryl carboxylic acids, such as trimellitic acid and pyromellitic acid, can be used as starting materials. Mixtures of the arylcarboxylic acids described in the above also are eligible for application of the method according to the invention.

The invention relates particularly to a method for the conversion of unsubstituted benzoic acid ($R_1$ through $R_5$=hydrogen) into the corresponding unsubstituted phenol.

The oxidation of the Cu-containing catalyst, with conversion of Cu(I) arylcarboxylate into Cu(II) arylcarboxylate, is a first reaction step in the process. It brings about an increase in the degree of oxidation of the copper (from 1+ to 2+), while an extra arylcarboxylate part is incorporated in the Cu-containing catalyst.

The process conditions for this need to be chosen according to the first embodiment of the invention such that on the one hand the reaction can be carried out in the liquid phase (i.e. above the melting point of the arylcarboxylic acid that is to be converted), but on the other at such a temperature that the following steps (viz. reduction and hydrolysis) are minimized. Thus, it is preferable to avoid temperatures above 190° C., and certainly those above 210° C., in the first process step to minimize tar formation. To even more avoid the following steps and to suppress side reactions, the catalyst oxidation is preferably carried out in the substantial absence of the phenol. However, at the lower reaction temperatures of 190° C. and less not much tar is formed even with 4-5% phenol present during oxidation. The presence of excess amounts of the phenol (for instance due to recycle flows) in the oxidation may give rise to the formation of tarry byproducts that adversely affect the overall selectivity.

It has now been found that oxidation temperatures higher than 190° C. and up to about 270° C. can be used with high selectivity of the desired phenol product and with little, if any, tar or other by-product formation. Thus, oxidation temperatures broadly ranging from about 120° C. to about 270° C. can be used according to the invention embodiments described herein. In addition, the invention can be carried out as a one-step or multi-step process under liquid phase or gas phase conditions.

The one-step process is preferably carried out at 210°-250° C. Although application of the inventions makes it possible to achieve a 10-20% higher selectivity than in the conventional Dow phenol process, some tar is still formed in the one-step process.

Therefore, it can be efficacious to remove part of the reactor mass and if desired free it of tar, after which copper and benzoic acid can be brought back into the process.

By keeping the Cu(I) concentration at a certain minimum value, the yield improves to more than 92%, preferably more than 95% (if measured at 1 bar).

In a one-step process according to the second embodiment of the invention the concentration of copper in the Cu(I) form preferably remains higher than 0.15 wt.%, in particular higher than 0.2 wt.%. The difference with the two-step process in respect of the Cu(I) concentration to be preferably applied is mainly a consequence of the hydrodynamic behavior of the reactor under these circumstances.

Surprisingly, it is found that formation of tar virtually does not occur.

The upper limit is not critical, but sufficient Cu(II) is advantageous in that it promotes a high productivity. Therefore the aim will be to have more than 50% copper oxidized to Cu(II).

Oxidation of Cu(I) to Cu(II) proceeds well particularly if carried out using an oxygen-containing gas. Air, whether or not enriched with or reduced in oxygen, is very suitable. Such a gas can be passed through the Cu-containing liquid, for instance in a bubble column, or through a fixed of Cu-containing catalyst as described in the third embodiment. The pressure applied is not critical, but in general an elevated pressure will be chosen so as to accelerate the oxidation process. Pressures of 0.1-2.5 MPa therefore are suitable.

An alternative and very suitable method for bringing about the conversion of Cu(I) into Cu(II) is to use the effect of an electrochemical potential, in which case the abstraction of an electron enables the desired copper conversion to take place.

It has been found that for the conversion of Cu(I) into Cu(II) using an oxygen-containing gas (or other means by which Cu oxidation can be effected via an oxygen group) preference is to be given to the use of a deficiency of oxygen relative to the amount of Cu(I) in the catalyst. Thus, it is ensured that not all of the Cu is in the Cu(II) form. It is particularly desirable to oxidize 30-95% of the Cu(II). For electrochemical conversion of Cu(I) to Cu(II) such a measure was found to be unnecessary.

The amount of Cu-containing catalyst is to be chosen so that on the one hand good activity is obtained, but on the other hand it should not be so large as to give rise to the presence of a separate, solid catalyst phase throughout the process. In the homogeneous process the catalyst is dissolved in the reaction mixture, though some excess in the oxidation step (where the temperature may be much lower than in the following step) is allowable. The copper concentration (as a metal) in the oxidation step therefore is 0.5-15 wt.%, more preferably 1-10 wt.%; and ideally the process is carried out using a copper concentration between 1.5 and 8 wt.% (all figures relating to the reaction mixture in the oxidation step).

The Cu-containing catalyst in the present process is essentially the Cu-complex with the aromatic carboxylic acid. Initially, copper can be added in virtually any form that dissolves in the aromatic carboxylic acid, such as copperoxide, coppersalts such as copper sulphate, copper nitrate, copper chloride and the like, Even copper metal can be used, if the conditions are properly chosen in order to prevent scaling of the reactor in the liquid phase embodiments.

There may be advantage in using a catalyst containing a co-catalyst besides copper. This co-catalyst can be chosen in particular from groups V, VI, VII and VIII as well as from the group of the lanthanides and actinides of the Periodic System of the Elements. These components affect the oxidative capacity of the Cu in the catalyst. Furthermore, promoters may be used, suitable substances being in particular (earth) alkaline metals, such as Mg or Li. Preferably, these co-catalyst and/or promoters are used in an amount of 0.1-10 wt.%, preferably 1-10 wt.%, based on the reaction mixture.

The second step in the method according to the invention comprises a combination of a reduction (yielding the aryl aryl carboxylate) and hydrolysis to the phenol, with carbon dioxide ($CO_2$) being separated. Here and hereafter aryl aryl carboxylate is understood to be a compound having the following structure where $\phi_1$ and $\phi_2$ is an aryl group, substituted or unsubstituted, as found in structure (I). When performing the reduction and hydrolysis step separately (as in NL-A-78.017199) first o-, m- and p-arylcarboxyl-aryl carboxylic acids are formed, which are the products of two aryl carboxylic acids coupled to one another. The o- and p-products are converted into the corresponding phenol by the subsequent hydrolysis. The m-products, which are formed in an amount of 25-50% of the products, cannot, under the indicated process conditions, be converted to the corresponding phenols.

It seems probable that the choice of process conditions in the second step according to the invention results in a strong suppression of the formation of the m- and p-products. The o-product is immediately, under the process conditions of the invention, converted into the corresponding phenol. If no water is applied in said reduction, undesirable byproducts are formed which cannot be converted into the corresponding phenol.

In contrast to what is stated in NL-A-78.07199, it thus has proved essential in the second step of the method according to the invention for water to be present in the reduction step. This makes it possible to combine this reduction into one process step with the subsequent hydrolysis step, in which water must necessarily be present. This can be done particularly well because the temperature at which this reduction is carried out is higher than that preferred in NL-A-78.07199 (which cites a temperature $\leq 220°$ C.). It has been found that the use of higher temperature gives rise to an improvement of the overall selectivity.

According to the invention the hydrolysis step yielding the phenol should take place at a temperature above about 210° C. and generally in the range of 225°-270° C. and preferably in the range of 235°-250° C. This temperature is significantly higher than that applied for hydrolysis in NL-A-70.00685, viz. about 200° C.

In the case of the two-step synthesis the process is preferably carried out under such conditions that the subsequent steps (viz. the reduction and formation of phenol) do not yet take place to any significant extent. At lower temperatures (e.g. 191°-200 C.) the oxidation step can take up to 20 minutes, at higher temperatures a shorter liquid retention time will be chosen. Preferably, the liquid retention time is 1-10 minutes.

It is preferred in particular in the case of a two-step synthesis according to the second embodiment to oxidize the Cu-containing catalyst in accordance with the process described above at a temperature of 210°-240° C.

The second reaction step in the process according to the second embodiment of the invention comprises reduction of the catalyst and formation of the phenol, with release of carbon dioxide ($CO_2$). In a one-step process of the second embodiment the same process conditions, hydrolysis and reduction, will in general be applicable as described above for the oxidation reaction step. As a rule, 0.3-5 wt.% water is present, preferably 0.5-3 wt.% during hydrolysis and reduction.

In the two-step process the second reaction step is preferably continued until 30-90% of the Cu(II) has been converted, in particular 60-90%.

Both the reduction and the hydrolysis take place in the absence of oxygen, which is in contrast to the process disclosed in NL-A-70.00685. Oxygen being absent, re-oxidation of the Cu-containing catalyst in this process step is avoided, so that there can be no, disadvantageous, reactions between the phenol, or intermediates thereof, and such an oxidized catalyst, which would give rise to the formation of selectivity-depressing byproducts, such as tar.

Before subjecting the oxidation reaction mixture to reduction and hydrolysis, it is advantageous to free the reaction mixture of part of the arylcarboxylic acid contained in it. The degree to which this is possible is determined by the solubility of the copper-containing catalyst in the reaction mixture under the process conditions of the second step. Partial evaporation (for instance by distillation) is one of the methods by which an amount of arylcarboxylic acid can be removed; this arylcarboxylic acid can, depending on its quality, be passed to the upgrading section (more on which later) or fed direct to the oxidation step.

It is advantageous to use such an amount of water during hydrolysis and reduction as to achieve virtual equimolarity relative to the amount of arylaryl carboxylate. As a result, the reaction product obtained upon completion of the hydrolysis is almost free of water, which is of advantage in further upgrading to pure phenol of the reaction product thus obtained.

The pressure under which hydrolysis and reduction is performed is not critical, but the advantage of raising the pressure to above atmospheric level is that has a favorable effect on the reaction kinetics and that the volatility of the reaction product is reduced. The pressure to be applied will generally be between 0.1 and 2.5 MPa; higher pressures, though allowable, do not yield substantial improvements of the process.

In accordance with the third embodiment (gas phase) of the invention, the oxidation step should be so performed that (virtually) no tar is formed. This can be achieved by various measures. For instance it can be ensured that no phenol is absorbed onto the catalyst. This can be accomplished by stripping with steam or an inert gas at the end of hydrolysis and reduction. Alternatively, the temperature of the catalyst bed during hydrolysis and reduction can be kept below 200° C., preferably between 150°-190° C. (because the rate of oxidation of Cu is high and tar formation does not occur until the temperature exceeds 200° C., in the presence of phenol). It is also possible to apply a higher temperature e.g., 191°-270° C. or higher and keep the contact time between the reaction mixture and the oxygen short, e.g. 0.1-5 minutes, so that not all the copper is converted into the Cu(II) form.

The Cu-containing catalyst for gas phase contacting can be supported by a carrier, comprising oxides of silicon, titanium, cadmium, or carbon and the like, as well mixtures thereof. Preferably, the catalyst is used immobilized on a carrier. Silica is preferably used as carrier. The catalyst load will as a rule be 5-40 wt.% copper metal on the carrier. A high degree of loading contributes to a high conversion per volume unit.

There may be advantage in using a catalyst containing a co-catalyst besides copper supported on a suitable carrier. This co-catalyst can be chosen in particular from groups III through VIII as well as from the group of the lanthanides and actinides of the Periodic System of the Elements. These components have an effect on the oxidative capacity of the Cu in the catalyst.

The catalyst used can comprise copper, zirconium and, if desired, an alkali metal or an alkali earth metal such as sodium, potassium, lithium or magnesium. Also, rare earths (atom numbers 37 through 71) or zirconium, silver, vanadium, chromium, molybdenum, hafnium and tungsten or mixtures thereof in combination with copper can be used.

Examples of suitable catalyst systems are described in EP-A-52839, EP-A-40452, NL-A-7810528, NL-B-110374 and NL-B-107561.

It is advantageous to use such an amount of steam during hydrolysis and reduction of the process according to the third embodiment of the invention as to achieve at least equimolarly thereof relative to the amount of Cu(II) benzoate. Preferably, some excess is applied, a two- to four-fold excess as a rule being sufficient to ensure a high yield.

The pressure under which the hydrolysis and reduction step is performed during gas phase contacting is not critical, but the advantage of raising the pressure to above atmospheric level is that it has a favorable effect on the reaction kinetics. The pressure to be applied will generally be between 0.1 and 2.5 MPa; higher pressures, though allowable, do not yield substantial improvements of the process.

The temperature during gas phase contacting in the first or oxidation step ranges from about 120°–350° C., in one embodiment preferably about 120°–190° C. to preclude tar formation by using a low temperature, in another embodiment preferably about 210°–350° C. to be able to use approximately the same temperature as in the second step in order to minimize heating and/or cooling. In the second or hydrolysis and reduction step the temperature ranges from about 210°–350° C., preferably 250°–350° C. The contact time will vary in both steps depending upon the temperature level but generally will be from about 0.1–5 minutes, with a residence time in the column of preferably 1–240 sec.

It can be advantageous to aftertreat the reaction mixture obtained following hydrolysis and reduction in order to promote the formation of phenol. This can be effected by using an acid ion exchanger in a fixed bed reactor.

The reaction products are subjected to an upgrading operation in order to separate and recover the phenol obtained. This can be done in ways known by themselves, for instance by distillation.

The bottom flow of the distillation, which may contain non-converted arylcarboxylic acid, can be recycled to the process, optionally after a purification step.

The catalyst in the gas phase embodiment can be used in the form of fixed or moving beds. The two-step reaction can be carried out intermittently, successively supplying for a short time an oxygen-containing gas to e.g. a fixed-bed reactor and then—with exclusion of oxygen—having the hydrolysis and reduction step take place. After the catalyst has been conditioned for the first step, the oxidative gas mixture can be supplied again. The two-step process can also be carried out continuously by having the oxidation step take place in the first reactor of a multiple reactor system and then bringing the catalyst, preferably in a moving bed, to a second reactor, where the hydrolysis and reduction step takes place. In that case the reactors can be fully adapted to the desired requirements.

The amount of Cu-containing catalyst employed during liquid phase oxidation is to be chosen so that a good activity is obtained, but preferably it should not be so large as to give rise to the presence of a separate, solid catalyst phase throughout the process. The catalyst is dissolved as Cu(I) salt in the reaction mixture. The copper concentration (as metal) in the oxidation step therefore is 4–10 wt.%, preferably 5–8 wt.% (all relative to the reaction mixture in the oxidation step). As the solubility of Cu(II) arylcarboxylate is lower than that of Cu(I) arylcarboxylate, the amount of Cu(II) salt comes to exceed the solubility product of that salt in that medium during the oxidation step. As a consequence, a precipitate of Cu(II) salt is formed.

For controlled slurry formation during liquid phase oxidation, nucleation agents are added according to the fourth embodiment of the invention. Preferably, the nucleating agent is Cu(II) benzoate which is added in solid form by way of a recirculation flow from a line leading to the reactor where hydrolysis and reduction is effected or from the first reactor where hydrolysis is effected. In this way, part of the slurry is recycled from hydrolysis to oxidation.

With respect to the nucleating agent for the fourth embodiment, basically Cu(II) benzoate (or substituted analogues) are strongly preferred agents. Since at these "high" Cu concentrations Cu(II) salts are crystallized, whereas Cu(I) salts are still soluble, the recirculation of a (small) proces-stream from the decomposition reactors to the oxidation reactor provides solid particles which are completely "compatible" in the process. Any other nucleating agent would be a proces-foreign compound, which could give rise to contamination.

The second step in the process according to the fourth embodiment of the invention comprises a combination of a reduction and the formation of the phenol, in which process carbondioxide ($CO_2$), is released. This step, in which the Cu(II) salt slurry is converted into Cu(I) salt and phenol, is carried out in a cascade of at least two reactors in order to prevent slipthrough of the Cu(II) salt particles as much as possible. Preferably three, in particular four reactors are used.

The second step is effected in such a manner that 30–90%, preferably 60–90%, of the Cu(II) salt is converted into Cu(I). This may take from 0.05 to 8 hours, depending on the temperature. Preferably the temperature is chosen so that a retention time of 0.1–3 hours is sufficient. A very high temperature in the second step entails the risk of formation of metallic copper, which is undesirable.

The conditions of temperature and pressure employed for oxidation and hydrolysis in this embodiment of the invention can be the same as used in the other liquid phase embodiments described above.

Figure 2:
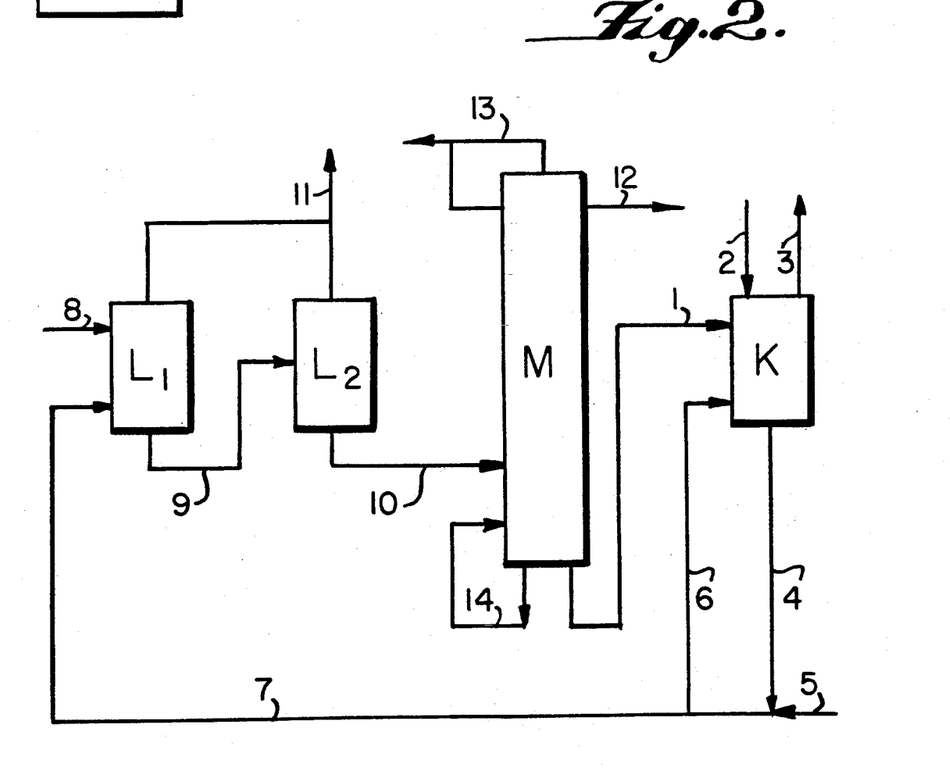
FIG. 2 is a schematic process flow diagram as described in the fourth embodiment for liquid phase oxidation of a Cu-containing catalyst in the presence of a nucleating agent and hydrolysis and reduction of the oxidized catalyst in a plurality of cascade reactors or reaction zones.

Referring to FIG. 2, K is the oxidation reactor, L1 and L2 are the decomposition and hydrolysis reactors and M is the phenol separation column.

Copper (I) benzoate is supplied to the oxidation reactor (K) via line (1). Via (2) and (3) air is led in and discharged, causing the copper to be oxidized. The Cu(II) benzoate crystallizes out and is supplied to the decomposition section $L_1$ via lines (4) and (7). Flow (6) is the recirculation flow, by which 1–20% of the effluent from reactor K is recycled from line (4) to reactor K, thereby providing the nucleating agent to the reactor. Fresh benzoic acid can be supplied via (5). Lines 4 through 7 are preferably kept at a temperature which is 1°–20° C., preferably 1°–10° C., higher than the temperature in K in order to prevent precipitation (scaling) of copper.

The decomposition reactors L1 and L2 are provided with a $CO_2$ offgas line (11) and a water supply line (8). The decomposition/ hydrolysis product removed from reactor $L_1$ is passed by line (10) to the phenol separation section M. Phenol is separated via (12), water is removed via (13). Line 14 represents a reboiler.

After the hydrolysis and reduction step the reaction mixture is subjected to an upgrading operation to separate and recover the phenol obtained as described in connection with FIG. 2. Certainly when hardly any water is left in the reaction mixture (in contrast to the process described in NL-B-90.684, which is also referred to as the 'wet route'), there is no longer any need to use an auxiliary material in the distillation (such as toluene to break the phenol-water azeotrope). The bottom flow of the distillation, containing non-converted arylcarboxylic acid and the Cu-containing catalyst, can be recycled to the oxidation step (reactor K), optionally after a purification step (separation column M).

The process according to the invention is particularly suitable for the preparation of unsubstituted phenol from unsubstituted benzoic acid. This phenol can be used, for instance, as a basic material for both phenol-formaldehyde resins and the preparation of caprolactam, the nylon-6 feedstock.

The invention will be elucidated in the following examples. However, these examples should not be construed as limiting the invention.

The following examples (I-XII) have been conducted in an oil-heated, double-walled reactor having an effective volume of 0.5 l. This reactor was provided with a stirrer, gas inlet, steam inlet, gas outlet and a distillation set-up. Use was made of a gas cylinder filled with a gas of a calibrated composition (nitrogen with 4.8 vol. % oxygen), to feed gas to the reactor. After cooling of the condensible products, the off-gas was analyzed for oxygen and carbon dioxide. In all runs, which were performed batchwise, use was made of 350 g of reactor mass, consisting of the desired amounts of catalyst, co-catalyst and promoter, with arylcarboxylic acid added up to the total weight. During the run no make-up supplies were made to the reactor mass. The catalyst, co-catalyst and promoter were supplied as the metal oxide or as the metal arylcarboxylate, with identical results in both cases.

Upon completion of the reaction, the reaction product obtained and the reactor mass were subjected to HPLC (High Pressure Liquid Chromatography) analysis. The results presented in Table I were obtained as follows:

a) the phenol yield (Σ F) is expressed as the number of moles obtained of phenol + aryl aryl carboxylate + p-arylcaraboxy arylcarboxylic acid + p-hydroxyaryl carboxylic acid;
b) the yield of m-product (Σ m-product) is expressed as the number of moles obtained of m-arylcarboxy arylcarboxylic acid +m-hydroxyaryl carboxylic acid;
c) the yield of total products (Σ products) is expressed as ΣF+m-products;
d) the selectivity towards phenol (SF) is expressed as $$\frac{\Sigma F}{\Sigma \text{ products}} \times 100\%$$

In none of the examples was formation of tar-like products observed, while in recycle examples V and VI no catalyst deactivation was observed. For all examples the mass, aromatic ring, $CO_2$ and $O_2$ balances had a value between 99% and 101%.

EXAMPLE I

The gas was passed through a reactor mass on the basis of 1.0 wt.% of Cu(I) in benzoic acid at a flow rate of 30 Nl/h during 18 minutes, the temperature being 180° C and the pressure 0.1 MPa. From the gas balance and the oxygen absorption derived from this balance, the conversion of Cu(I) to Cu(II) was found to be 95%.

EXAMPLE II

Example I was repeated, now 3.0 wt.% of Cu(II) being used. After the oxidation a combined reduction and hydrolysis (second step) was performed. To this end 30 g/h of water was supplied; the reaction was carried out at a temperature of 230° C. and a pressure of 0.1 MPa. EXAMPLE III In this example the conditions of Example II were maintained except that the temperature of the second step now as 240° C.

EXAMPLE IV

In this example the reactor mass contained, besides benzoic acid, 3.0 wt.% of Cu(II) and 3.5 wt.% of Mg (II), the further process conditions being as in Example II.

EXAMPLE V

Example II was repeated, and upon completion fresh benzoic acid was added to the reactor mass obtained, which was then subjected to an oxidation step in which 30 Nl/h of the gas was passed through during 18 minutes, at a temperature of 170° C., following which the second step was performed again. This was repeated 3 times.

EXAMPLE VI

Example IV was repeated, and upon completion fresh benzoic acid was added to the reactor mass obtained, which was then subjected during 18 minutes to an oxidation step at a temperature of 180° C. 30 Nl/h of air was passed through. After this, the second step was performed again. This was repeated 5 times.

EXAMPLE VII

The reactor mass of Example V was subjected to a supplementary hydrolysis reaction during 20 hours by feeding 30 g/h water at 230° C. and a pressure of 0.1 MPa to check if further conversion of the m-products still present into the phenol is possible.

The results of the examples I-VII are summarized in the following Table 1.

TABLE 1

| | | | | Results | | |
|---|---|---|---|---|---|---|
| No. | time h | temp. °C. | pressure $10^5$ Pa | Σ F mmol | Σm-products mmol | SF % |
| I | 0,3 | 180 | 1,0 | 0 | 0 | 0 |
| II | 4,0 | 230 | 1,0 | 73 | 9 | 89,0 |
| III | 4,0 | 240 | 1,0 | 75 | 7 | 91,5 |
| IV | 4,0 | 230 | 1,0 | 83 | ≦1 | ≧99 |
| V | 0,3 4,0 | 170 230 | 1,0 | 208 | 15 | 93.3 |
| VI | 0,3 4,0 | 180 230 | 1,0 | 408 | ≦1 | ≧99 |
| VII | 20 | 230 | 1,0 | 208 | 15 | 93.3 |

COMPARATIVE EXAMPLE A

Example I of NL-A-78.07199 was repeated at a temperature of 218° C. and during an experimental period of 1 hour, the Cu(II) concentration, for obtaining a homogeneous catalyst application, being 4.0 mol %.

COMPARATIVE EXAMPLE B

The preceding example A, was repeated, but now during a period of 2 hours.

COMPARATIVE EXAMPLE C

Comparative example B was repeated, use being made also of 3.5 wt.% Mg (II).

COMPARATIVE EXAMPLE D

An attempt was made to repeat Example III of NL-A-78.07199, but under the conditions as specified there it proved impossible, at atmospheric pressure, to obtain a temperature above 150° C., so that no phenol formation reaction occurred. By adjusting the xylene content to 10 wt.% relative to the reactor mass the temperature could be raised to 215° C. The further conditions of this comparative example are the same as those of comparative example A.

In the following the results are presented of examples using substituted benzoic acids. In all cases both reaction steps were analogous to those of Example II. The Cu (II) concentration was 4.0 mol %.

EXAMPLES VIII AND XII

Analogous to Example II, in the examples m-methyl benzoic acid and m-dimethyl amino benzoic acid, respectively, were used as starting material. Also, use was made of 3.5 wt.% Mg (II).

EXAMPLES IX-XI

In these examples p-t-butyl benzoic acid, m-Cl-benzoic acid and m-$NO_2$-benzoic acid, respectively, were used as starting materials, the further process conditions being analogous to those of Example II.

When Example IX was repeated, the presence of 3.5 wt. % Mg (II) appeared to lead to a lowering of the reaction velocity, but not to a different selectivity.

The results of Comparative examples A-D and Examples VIII-XII are presented in Table 2.

TABLE 2

| | | | | Results | | |
|---|---|---|---|---|---|---|
| | time | temp. | pressure | ΣF | Σ-m-product | SF |
| No. | h | °C. | $10^5$ Pa | mmol | mmol | % |
| A | 1.0 | 218 | 1.0 | 46 | 35 | 56,8 |
| B | 2.0 | 218 | 1.0 | 47 | 37 | 56,0 |
| C | 2.0 | 218 | 1.0 | 100 | 34 | 74,6 |
| D | 1.0 | 218 | 1.0 | 100 | 102 | 49,5 |
| VIII | 1.0 | 230 | 1.0 | 132 | <1 | >99 |
| IX | 1.0 | 230 | 1.0 | 126 | <1 | >99 |
| X | 1.0 | 230 | 1.0 | 51 | <1 | >99 |
| XI | 1.0 | 230 | 1.0 | 106 | <1 | >99 |
| XII | 1.0 | 250 | 1.0 | 23 | 2 | 92,0 |

From this table it can be concluded that:
*)under the process conditions of NL-A-78.07199 a large amount of m-product is formed, so that the selectivity towards the desired product is low;
*)substituted benzoic acids, too, can according to the invention be converted into the corresponding phenols at high selectivities.

EXAMPLES (SECOND EMBODIMENT)

The following examples (XIII-XVII) have been conducted in an oil-heated, double-walled reactor having an effective volume of 0.5 l. This reactor was provided with a stirrer, gas inlet, steam inlet, gas outlet, distillation set-up, sampling point and reactor mass tapping point. For the comparative examples, use was made of a gas cylinder filled with a gas of a calibrated composition (nitrogen with 4.8 vol.% oxygen) to feed gas to the reactor. After cooling of the condensible products, the off-gas was analyzed for oxygen and carbon dioxide. In all runs, performed batchwise, use was made of 350 g of reactor mass, consisting of the desired amounts of catalyst, co-catalyst and promoter, with arylcarboxylic acid added up to the total weight.

The catalyst, co-catalyst and promoter were supplied as the metal oxide or as the metal arylcarboxylate, with identical results in both cases.

The conversion of Cu(I) to Cu(II) in oxidation reactions was determined in two ways: a) by direct analysis of Cu(I), Cu(II) and total Cu in the reactor mass, and b) by drawing up a gas balance across the oxidation.

The conversion of Cu(II) to Cu(I) in the decomposition/hydrolysis reactions was also determined in two ways: a) by direct analysis of Cu(I), Cu(II) and total Cu in the reactor mass, and b) from the sum of all (auto)-coupling products of an arylcarboxylic acid. These products were analyzed by HPLC. The conversions determined in this way were in good agreement (the deviation was less than 1%).

The results stated in the following description of the runs were obtained as follows:

a) The yield of phenol (ΣF) is expressed as the total of moles of phenol+phenylbenzoate+p-phenylcarboxybenzoic acid+p-hydroxybenzoic acid obtained.
b) The yield of m-product (Σm-product) is expressed as the total of moles of m-phenylcarboxybenzoic acid+m-hydroxybenzoic acid obtained (only relevant for comparative examples H-K).
c) The yield of total products (Σproducts) is expressed as ΣF+Σm-product+by-products.
d) the selectivity to phenol ($S_1$) is expressed as ΣF/Σ products ×100%.

The mass, aromatic ring, $CO_2$ and $O_2$ balances had a value of 99 to 101% for all examples.

EXAMPLES XIII-XIV AND COMPARATIVE EXAMPLES E AND F

A solution of Cu(I) benzoate in benzoic acid was oxidized to a certain degree. Then the solution of Cu(II) benzoate thus obtained was decomposed and hydrolyzed at a suitable temperature. The resulting phenol was distilled off to about 1% (w/v) and the solution was filled up with fresh benzoic acid to the original weight. Then the solution was oxidized again, etc. The cycle was completed at least five times.

The results are given in Table 3.

TABLE 3

| No. | oxidation T (°C.) | decomp./hydrolysis (°C.) | (co-)cat (% metal) | $S_f$ | [Cu(I)] oxid. end % (w/v) |
|---|---|---|---|---|---|
| XIII | 200 | 230 | 1% Cu, 3.5% Mg | 100% | 0.05% |
| E | 200 | 230 | 1% Cu, 3.5% Mg | 91% | <0.005% |
| XIV | 225 | 225 | 4% Cu, 2% Mg | 100% | 0.07% |
| F | 225 | 225 | 4% Cu, 2% Mg | 88% | <0.005% |

EXAMPLES XV-XVII AND COMPARATIVE EXAMPLE G

A solution as described above was simultaneously oxidized, decomposed and hydrolyzed. The resulting phenol was continuously distilled off to above 1% (w/v). the solution was filled up with fresh arylcarboxylic acid to the original weight. The run was continued for at least 7 hours.

The results are given in Table 4.

TABLE 4

| No. | Reactor Mass T (°C.) | (CO-)cat(M %) (% metal) | $S_f$ | [Cu(I)], average (% metal) |
|---|---|---|---|---|
| G | 242 | 1% Cu, 3.5% Mg | 88% | 0.11% |
| XV | 242 | 2% Cu, 3.5% Mg | 92% | 0.18% |
| XVI | 225 | 3% Cu, 3.5% Mg | 97% | 0.24% |
| XVII[a] | 230 | 4% Cu, 2% Mg | 98% | 2.12% |

[a]Also strongly reduced gas load relative to examples G, XV and XVI.

COMPARATIVE EXAMPLE H

Example I of NL-A-78.07199 was duplicated at a temperature of 218° C. for 1 hour. The Cu(II) concentration required for a homogeneous catalyst application was 4.0 mol%.

COMPARATIVE EXAMPLE I

Example E was repeated, but now for a period of 2 hours.

COMPARATIVE EXAMPLE J

Comparative example F was repeated, with 3.5 wt.% Mg (II) being additionally applied.

COMPARATIVE EXAMPLE K

It was attempted to duplicate example III of NL-A-78.07199; under the conditions specified therein it appeared to be impossible, at atmospheric pressure, to raise the temperature above 150° C., so that no formation of phenol occurred. By adapting the xylene content to 10 wt.% relative to the reactor mass it was possible to raise the temperature to 215° C. Further conditions of this comparative experiment G are analogous to those of comparative experiment D.

The results of comparative examples H-K are given in Table 5.

TABLE 5

| No. | time (hrs) | temp. (°C.) | pressure ($10^5$ Pa) | $\Sigma F$ (mmole) | $\Sigma$m-product (mmole) | $S_f$ % |
|---|---|---|---|---|---|---|
| H | 1.0 | 218 | 1.0 | 46 | 35 | 56.8 |
| I | 2.0 | 218 | 1.0 | 47 | 37 | 56.0 |
| J | 2.0 | 218 | 1.0 | 100 | 34 | 74.6 |
| K | 1.0 | 218 | 1.0 | 100 | 102 | 49.5 |

As appears from these tests, separate performance of the reduction and hydrolysis steps, as specified in NL-A-78.07199, results first of all in the formation of o-, m- and phenylbenzoates, which are the coupling products linking two arylcarboxylic acids with each other. The o- and p-products are evidently converted into the corresponding phenols in the subsequent hydrolysis. The resulting m-products, constituting 25-50% of the resulting products, cannot be converted into the corresponding phenols under the stated process conditions.

EXAMPLE XVIII (THIRD EMBODIMENT)

Figure 1:
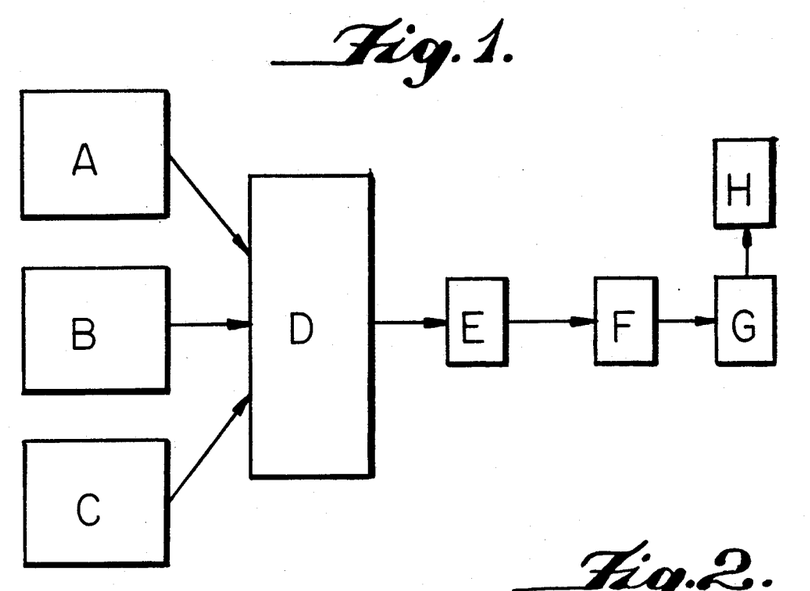
FIG. 1 is a schematic process flow diagram as described in the third embodiment for gas phase oxidation of a Cu-containing catalyst and hydrolysis and reduction of the oxidized catalyst with steam.

Gas phase tests were performed using a set-up as represented in FIG. 1, in which A represents a steam-generating device ($H_2O/N_2$ mixture), B a benzoic acid evaporator and C an air supply device. The three flows from each of A, B and C go to the reactor bed in D. The effluent from reactor D is passed through a series of coolers E, F and G, cooling the reaction mixture to 130° C., 8° C. and −80° C., respectively. H is the analysis section for the offgas mixture. The reactor consisted of a packed bed of about 2.5 ml, filled with copperoxide on silica. The gas flows from A, B and C were adjustable, products in E through H were analyzed using gas chromatography (GC) and high-pressure liquid chromatography (HPLC).

EXAMPLE XIX

The catalyst was oxidized with air for 30 seconds. Next, benzoic acid and steam were supplied for 240 seconds. The catalyst bed had a temperature of 250° C. The retention time of the acid and the steam on the columns was 4 seconds. The conversion of the benzoic acid was 20%. At the end of the cycle, only steam was supplied for 2 seconds in order to strip off adsorbed phenol. The selectivity to phenol was 96%, to benzene 4%. After five cycles the catalyst was extracted with ether. HPLC analysis showed that no tar products had formed on the catalyst.

EXAMPLE XX

Analogously to example XIX, so much steam and benzoic acid was supplied for 60 seconds at 300° C. that the retention time on the column was 2 seconds. The conversion was 40%, the selectivity to phenol was 91%, to benzene 9%. No tar was formed.

EXAMPLE XXI (FOURTH EMBODIMENT)

In a set-up as described in connection with FIG. 2, an oxygen-containing gas mixture was led through reactor K at 180° C., a copper concentration of 7.5 wt.% and a magnesium concentration of 0.5 wt.% in benzoic acid. The $O_2$ concentration varied between 1 and 15 vol.% and was so controlled that 0.05 wt.% copper remained present as Cu(I). The result in reactor K was a 35% slurry. Lines 4 through 7 had a temperature of 190° C. and the recirculation flow in line 6 was 2% of the flow in line 4. The temperature in the two decomposition/hydrolysis reactors $L_1$ and $L_2$ was 230° C. The retention time was such that the reaction mixture in line 10 was a homogeneous solution of mainly Cu(I) benzoate in benzoic acid and phenol. About five cycles were performed, in which no scaling (deposit of copper in the lines) or clogging occurred. The selectivity to phenol was 100%. If no recirculation flow by line 6 was supplied to reactor A, acute clogging occurred in the gas inlet system. If the temperature in lines 4 through 7 was 180° C. instead of 190° C., 13% scaling had occurred after five cycles (i.e. 13% of the copper had deposited in the lines).

EXAMPLE XXII

This example was performed analogously to example XXI; the temperature in reactors K, $L_1$ and $L_2$ was 225° C. A 7% slurry was formed in reactor K. The flow in recirculation line 6 was 10% of the flow in line 4. The temperature in the lines was 226° C. The selectivity to phenol was 100% and no clogging, nor scaling occurred. If no recirculation flow was carried out, the temperature in the oxidation section became unstable and the gas inlet tube was clogged after three cycles. Besides Cu(I) benzoate, carbonized products appeared to be present in the system. If lines 4 through 7 were kept at the same temperature as the reactors (225°), 2% of the copper had deposited in the lines after five cycles.

What is claimed is:

1. A process for the preparation of phenol in high yield and selectivity with substantially no tar formation by an oxidative decarboxylation of a corresponding arylcarboxylic acid having the formula wherein $R_1$ through $R_5$ can be hydrogen, $C_1$–$C_6$ alkyl, cycloalkyl, aryl, aryalkyl, amino, halogen and nitro acid and wherein at least $R_1$ or $R_5$ is hydrogen in the presence of a Cu-containing catalyst in which the Cu concentration as a metal and relative to the reaction mixture amounts to 0.5–15 wt.% and in which the degree of oxidation of the copper can be $1^+$ and $2^+$ which comprises (a) oxidizing the catalyst at a temperature above the melting point of the arylcarboxylic acid with the temperature, retention time, oxidation agent, arylcarboxylic acid concentration and Cu(I) concentration being controlled so that virtually no tar is formed, (b) reacting the oxidized catalyst in the presence of water, but in the absence of oxygen, to form a phenol, and (c) separating the phenol formed.

2. A method for the preparation of a phenol according to claim 1 by oxidative decarboxylation in the liquid phase of the corresponding arylcarboxylic acid in the presence of a dissolved Cu-containing catalyst, the phenol being obtained through a hydrolysis step, which comprises the following process steps:

(a) oxidizing the catalyst at a temperature of 120°–190° C.;

(b) reacting the aryl carboxylic acid with the oxidized catalyst of step (a), carried out in the absence of oxygen and with the aid of water, at a temperature of 225°–270° C.;

(c) separating of phenol thus obtained and recycling of reducing catalyst to step (a).

3. A method according to claim 2, wherein an oxygen-containing gas is used for the catalyst oxidation in a) and wherein the oxidation is carried out using a deficiency of oxygen relative to the amount of Cu in the catalyst.

4. A method according to claim 2, wherein the catalyst oxidation is carried out with an electrochemical potential.

5. A method according to claim 2 wherein the Cu-containing catalyst also contains a co-catalyst chosen from alkaline earth metals, groups V, VI, VII, VIII, lanthanides and actinides of the Periodic System of the Elements.

6. A method according to claim 2, wherein step (a) is carried out at a temperature of 150°–180° C. and wherein step (b) is carried out at a temperature of 230°–250° C.

7. A method according to claim 2, wherein the concentration of copper as a metal and relative to the reaction mixture in the oxidation step amounts to 1–10 wt.% and wherein step (b) is carried out using an amount of water that is virtually equimolar relative to the amount of arylarylcarboxylate.

8. A method according to claim 2, wherein unsubstituted benzoic acid is used as arylcarboxylic acid.

9. A process for the preparation of a phenol by an oxidative decarboxylation in a liquid phase of a corresponding arylcarboxylic acid wherein $R_1$ through $R_5$ can be hydrogen, $C_1$–$C_6$ alkyl, cycloalkyl, aryl, aryalkyl, amino, halogen and nitro acid and wherein at least $R_1$ or $R_2$ is hydrogen in the presence of a Cu-containing catalyst in which the degree of oxidation of the copper can be $1^+$ and $2^+$, wherein the oxidative decarboxylation is carried out (i) in the presence of water, (ii) with an amount of oxygen being added such that an amount of copper remains present as Cu(I) so that a selectivity to phenol of more than 92% measured at 1 bar is obtained, and (iii) phenol is separated off.

10. A process according to claim 9, wherein the oxidative decarboxylation is carried out at 210°–250° C. and wherein at least 0.15 wt.% copper remains present as Cu(I).

11. A process according to claim 1 for the preparation of a phenol by an oxidation decarboxylation in a liquid phase of a corresponding arylcarboxylic acid in the presence of a Cu-containing catalyst, which comprises the following process steps:

(a) oxidizing the catalyst at an elevated temperature under oxidation conditions for at most 20 minutes, with such an amount of oxygen being added that at least 0.04 wt.% copper remains present as Cu(I);

(b) reacting oxidized catalyst of step (a) in the absence of oxygen, but in the presence of water, to form the phenol; and (c) separating phenol and recycling of reduced catalyst to step (a).

12. A process according to claim 11, wherein the oxidation of the catalyst is carried out with a gas containing 1–15% oxygen and wherein the oxidation is carried out in 3–10 minutes.

13. A process according to claim 11, wherein the Cu-containing catalyst additionally contains a co-catalyst chosen from alkaline earth metals, groups V, VI, VII, VIII, lanthanides and actinides of the Periodic System of the Elements.

14. A process according to claim 11, wherein step (a) is carried out at a temperature of 210°–240° C.

15. A process according to claim 11, wherein the copper concentration as metal and relative to the reaction mixture amounts to 1–10 wt.%.

16. A process according to claim 11, wherein step (b) is carried out with a virtually equimolar amount of water relative to the amount of Cu(II) and wherein step (b) is carried out at a temperature of 220°–250° C.

17. A process according to claim 11, wherein step (a) and step (b) are carried out at approximately the same temperature.

18. A process according to claim 11, wherein an unsubstituted benzoic acid is used as arylcarboxylic acid.

19. A process according to claim 1 for the preparation of a phenol by oxidative decarboxylation in a gas phase of a corresponding arylcarboxylic acid in the presence of a Cu-containing catalyst, which comprises the following process steps:
   (a) contacting a bed of Cu-containing catalyst under gas phase oxidation conditions with an oxidant-containing gas mixture under conditions that tar formation is virtually absent, and
   (b) contacting oxidized catalyst of step (a) with arylcarboxylic acid and steam under gas phase conditions with exclusion of oxygen, resulting in formation of gaseous phenol.

20. A process according to claim 19, wherein the oxidation of the catalyst in step (a) is carried out with an oxygen-containing gas and wherein the oxidation is carried out with a deficiency of oxygen relative to the amount of Cu in the catalyst.

21. A process according to claim 19, wherein the Cu-containing catalyst also contains a co-catalyst chosen from alkaline earth metals, groups V, VI, VII, VIII, lanthanides and actinides of the Periodic System of the Elements.

22. A process according to claim 19, wherein the catalyst contacted in step (a) contains virtually no phenol.

23. A process according to claim 19, wherein at the end of step (a), phenol present is stripped from the catalyst.

24. A process according to claim 19, wherein the temperature of the catalyst bed is about 120°–250° C. during step (a) and wherein step (a) takes about 0.1–5 minutes.

25. A process according to claim 19, wherein step (b) is carried out with about an equimolar amount of steam relative to the amount of Cu(II) and wherein step (b) is carried out at a temperature of about 210°–350° C.

26. A process according to claim 19, wherein an arylcarboxylic acid is used as unsubstituted benzoic acid.

27. A process according to claim 1 for the preparation of a phenol by an oxidative decarboxylation n a liquid phase reaction mixture of a corresponding arylcarboxylic acid in the presence of a Cu(I)-containing catalyst, which comprises the following process steps:
   (a) oxidizing of the catalyst with the temperature, retention time, oxidation agent, phenol concentration and Cu(I) concentration being chosen so that virtually no tar is formed, and wherein 4–10 weight % Cu is present in the reaction mixture and that such a quantity of Cu(I) salt is converted to Cu(II) salt that the quantity of Cu(II) salt is higher than its solubility product so that a slurry is formed,
   (b) adding a nucleating agent to step (a) for crystallization and controlling slurry formation,
   (c) reacting the oxidized catalyst containing nucleating agent of step (b) with water in the absence of oxygen in a cascade of at least two reaction zones to form a phenol, and wherein reduction of the catalyst is continued until a homogeneous solution is obtained, and
   (d) separating phenol and recycling reduced catalyst to step (a).

28. A process according to claim 27, wherein the oxidation of the catalyst is carried out with an oxygen-containing gas.

29. A process according to claim 27, wherein part of the slurry is recycled from step (c) to step (a).

30. A process according to claim 27, wherein the oxidation is carried out by an electrochemical potential.

31. A process according to claim 27, wherein the Cu-containing catalyst contains a co-catalyst chosen from alkaline earth metals, groups V, VI, VII, VIII, lanthanides and actinides of the Periodic System of the Elements.

32. A process according to claim 27, wherein step (a) is carried out at a temperature of about 120°–270° C.

33. A process according to claim 27, wherein the oxidation in step (a) is carried out with such a quantity of oxygen being supplied that at least 0.04 wt.% copper remains present as Cu(I) salt.

34. A process according to claim 33, wherein that step (a) is carried out at a temperature between 210°–250° C.

35. A process according to claim 33, wherein step (c) is carried out with a virtually equimolar quantity of water relative to the quantity of Cu(II).

36. A process according to claim 33, wherein step (c) is carried out in a cascade of four reaction zones.

37. A process according to claim 33, wherein step (c) is carried out at a temperature of 220°–250° C.

38. A process according to claim 33, wherein the arylcarboxylic acid used is unsubstituted benzoic acid.

39. A process according to claim 27 wherein the nucleating agent is copperbenzoate.

* * * * *